United States Patent
Carbunaru et al.

(10) Patent No.: US 8,543,216 B2
(45) Date of Patent: *Sep. 24, 2013

(54) CHARGING AND COMMUNICATION SYSTEM FOR A BATTERY-POWERED MICROSTIMULATOR

(75) Inventors: Rafael Carbunaru, Sherman Oaks, CA (US); Robert D. Ozawa, Woodland Hills, CA (US); Kenneth A. McGiboney, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/442,913

(22) Filed: Apr. 10, 2012

(65) Prior Publication Data

US 2012/0197352 A1 Aug. 2, 2012

Related U.S. Application Data

(62) Division of application No. 12/849,473, filed on Aug. 3, 2010, now Pat. No. 8,185,212, which is a division of application No. 10/609,449, filed on Jun. 27, 2003, now abandoned.

(60) Provisional application No. 60/392,475, filed on Jun. 28, 2002.

(51) Int. Cl.
*A61N 1/365* (2006.01)
(52) U.S. Cl.
USPC ............................................................ 607/61
(58) Field of Classification Search
USPC ............................................................ 607/61
See application file for complete search history.

(56) References Cited

U.S. PATENT DOCUMENTS 3,727,616 A * 4/1973 Lenzkes ........................ 607/59
4,082,097 A * 4/1978 Mann et al. ................... 607/33
(Continued)

FOREIGN PATENT DOCUMENTS

| WO | 97/18857 | 5/1997 |
| WO | 00/01320 | 1/2000 |
| WO | 02/09808 | 2/2002 |

OTHER PUBLICATIONS

Cameron, et al., "Micromodular Implants to Provide Electrical Stimulation of Paralyzed Muscles and Limbs," IEEE Transactions on Biomedical Engineering, vol. 44, No. 9, (Sep. 1997), pp. 781-790.

(Continued)

*Primary Examiner* — Rex R Holmes
(74) *Attorney, Agent, or Firm* — Wong, Cabello, Lutsch, Rutherford & Brucculeri, LLP

(57) ABSTRACT

A system and method are provided for both recharging and communicating with a stimulator having a rechargeable battery, which stimulator is implanted deeply in the body, in particular where the stimulator is a microstimulator, the system includes a base station and an external device, for instance a chair pad. The chair pad may contain an antenna/charging coil and a booster coil. The antenna/charging coil can be used for charging the rechargeable battery and also for communicating with the stimulator using frequency shift keying and on-off keying. The booster coil can be used to recharge a battery depleted to zero volts. The base station connected to the chair pad may be used to power the antenna/charging coil and the booster coil.

16 Claims, 9 Drawing Sheets

(56) References Cited

U.S. PATENT DOCUMENTS

| | | |
|---|---|---|
| 4,134,408 A | 1/1979 | Brownlee et al. |
| 4,561,443 A | 12/1985 | Radford et al. |
| 5,193,539 A | 3/1993 | Schulman et al. |
| 5,193,540 A | 3/1993 | Schulman et al. |
| 5,312,439 A | 5/1994 | Loeb |
| 5,405,367 A | 4/1995 | Schulman et al. |
| 5,642,030 A | 6/1997 | Seelye |
| 5,674,265 A | 10/1997 | Deschamps et al. |
| 5,750,926 A | 5/1998 | Schulman et al. |
| 5,769,877 A | 6/1998 | Barreras, Sr. |
| 5,807,397 A | 9/1998 | Barreras |
| 5,861,019 A | 1/1999 | Sun et al. |
| 6,032,076 A | 2/2000 | Melvin et al. |
| 6,051,017 A | 4/2000 | Loeb et al. |
| 6,061,596 A | 5/2000 | Richmond et al. |
| 6,073,050 A | 6/2000 | Griffith |
| 6,148,235 A | 11/2000 | Kuiper |
| 6,164,284 A | 12/2000 | Schulman et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,212,430 B1 | 4/2001 | Kung |
| 6,212,431 B1 | 4/2001 | Hahn et al. |
| 6,214,032 B1 | 4/2001 | Loeb et al. |
| 6,259,937 B1 | 7/2001 | Schulman et al. |
| 6,315,721 B2 | 11/2001 | Schulman et al. |
| 6,366,817 B1 | 4/2002 | Kung |
| 6,400,991 B1 | 6/2002 | Kung |
| 6,424,867 B1 | 7/2002 | Snell et al. |
| 6,434,194 B1 * | 8/2002 | Eisenberg et al. ............ 375/238 |
| 6,553,263 B1 | 4/2003 | Meadows et al. |
| 6,567,703 B1 | 5/2003 | Thompson et al. |
| 6,681,135 B1 | 1/2004 | Davis et al. |
| 7,107,103 B2 | 9/2006 | Schulman et al. |
| 7,167,756 B1 | 1/2007 | Torgerson et al. |
| 7,428,438 B2 * | 9/2008 | Parramon et al. .............. 607/61 |
| 8,185,212 B2 * | 5/2012 | Carbunaru et al. ............ 607/61 |
| 2002/0055779 A1 | 5/2002 | Andrews |
| 2002/0058971 A1 | 5/2002 | Zarinetchi et al. |
| 2003/0078634 A1 * | 4/2003 | Schulman et al. ............ 607/61 |
| 2003/0171792 A1 | 9/2003 | Zarinetchi et al. |

OTHER PUBLICATIONS

Loeb, et al., "North Sea: Transducers and Electrodes—Injectable Microstimulator for Functional Electrical Stimulation," Med. & Biol. Eng. & Computer, North Sea Special Feature, (Nov. 29, 1991), pp. NS13-NS19.

Loeb, et al., "BION™ Bionic Neurons for Functional and Therapeutic Electrical Stimulation," 20th Annual International Conference of IEEE Engineering in Medicine and Biology "Biomedical Engineering Towards the Year 2000 and Beyond," Oct. 29-Nov. 1, (1998), Hong Kong, 5 pages.

* cited by examiner

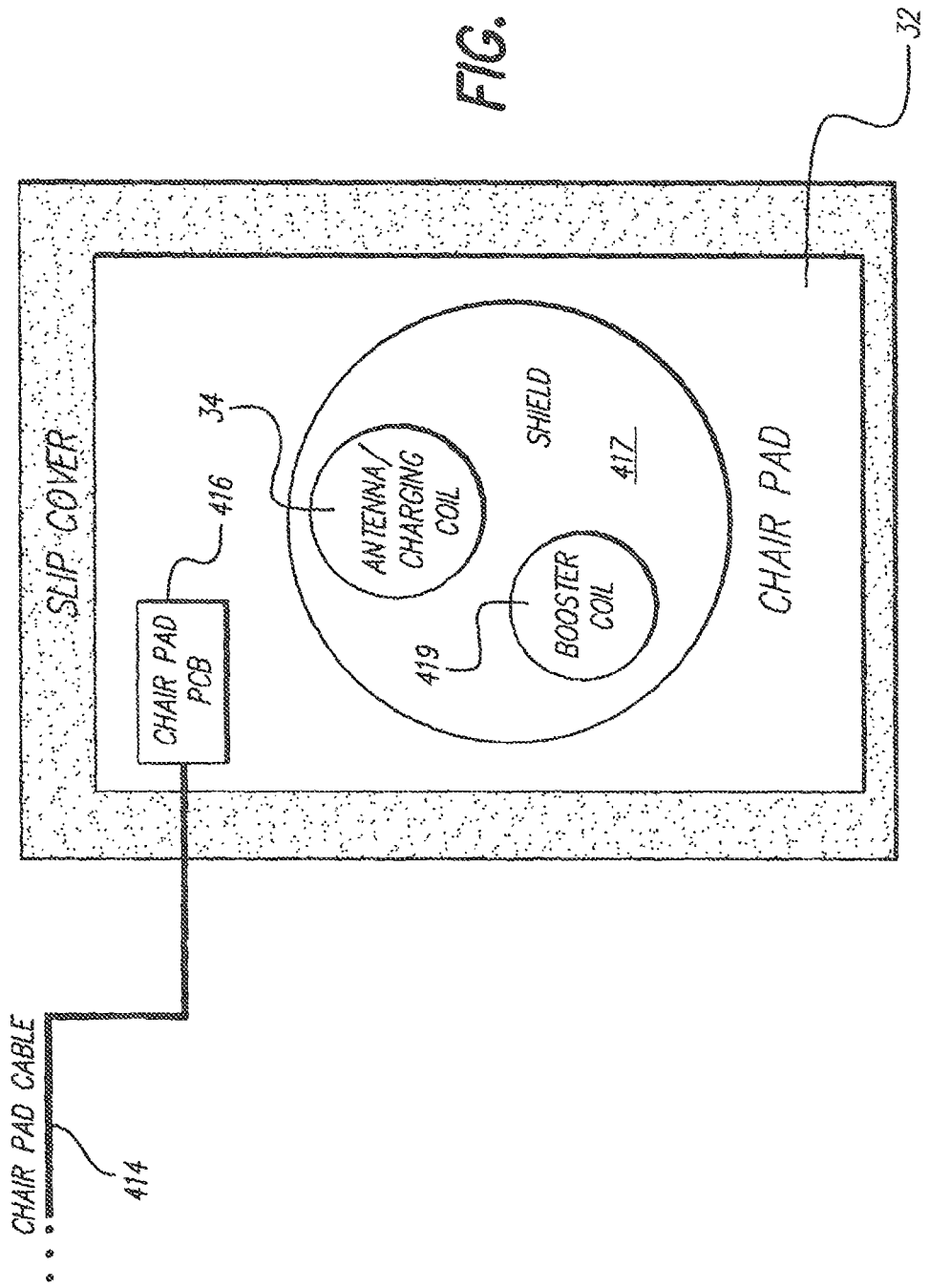

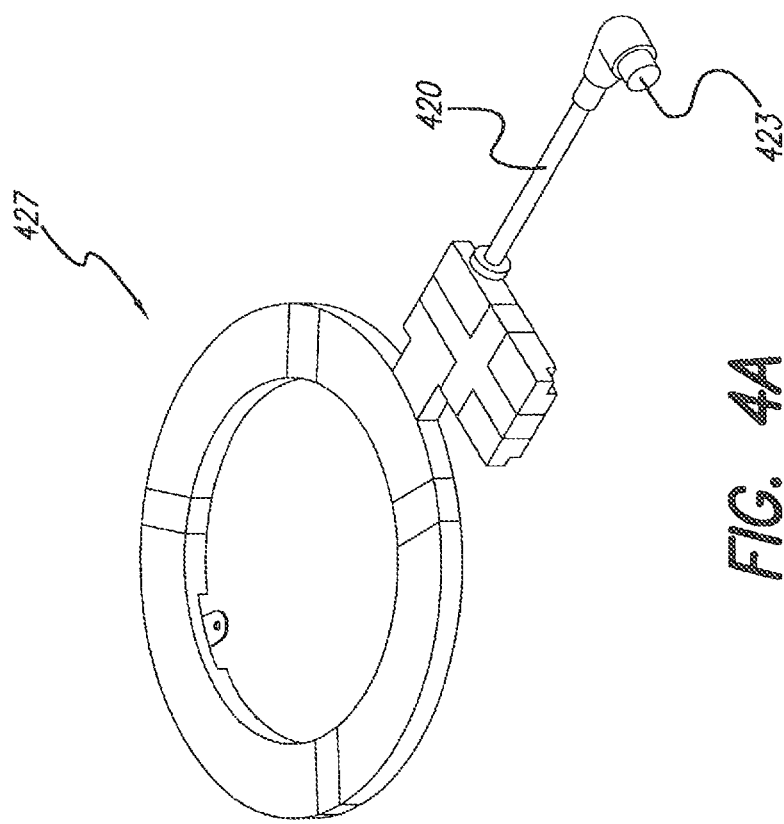

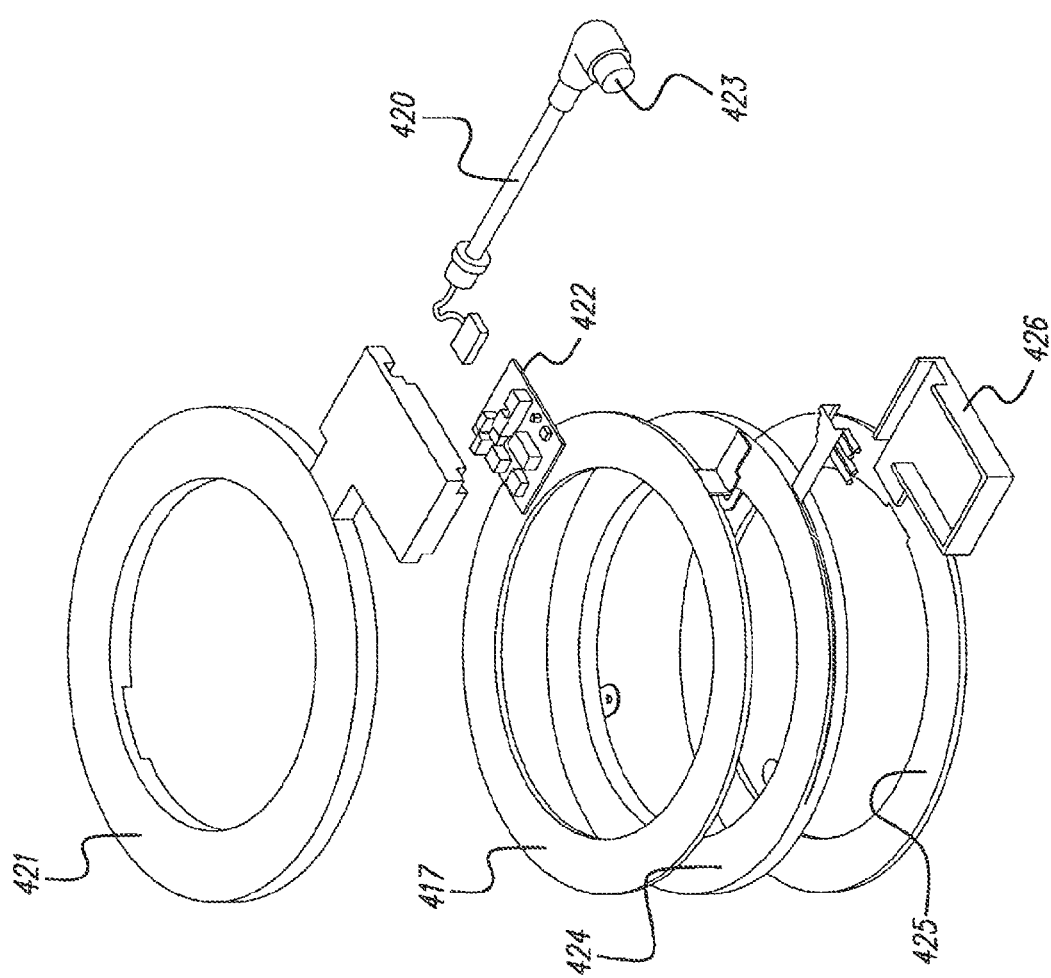

CHARGING AND COMMUNICATION SYSTEM FOR A BATTERY-POWERED MICROSTIMULATOR

This is a divisional of U.S. patent application Ser. No. 12/849,473, filed Aug. 3, 2010, now U.S. Pat. No. 8,185,212, which is a divisional of U.S. patent application Ser. No. 10/609,449, filed Jun. 27, 2003 (abandoned), which was a non-provisional filing of U.S. Provisional Application Ser. No. 60/392,475, filed Jun. 28, 2002. Priority is claimed to these applications, and these applications are incorporated herein by reference in their entireties.

BACKGROUND OF THE INVENTION

The present invention relates to stimulation systems and, more particularly, systems for transcutaneously charging and communicating with a body-implanted stimulator having a rechargeable battery.

Radio-frequency powered implantable stimulators and battery powered, implantable microstimulators are described in the art. See, for instance, U.S. Pat. No. 5,193,539 ("Implantable Microstimulator); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. Nos. 6,164,284 and 6,208,894 (both titled "System of Implantable Device for Monitoring and/or Affecting Body Parameters"). The '539, '540, '439, '452, '284, and '894 patents are incorporated herein by reference in their entireties.

Microstimulators to prevent or treat various disorders associated with prolonged inactivity, confinement or immobilization of one or more muscles are taught, e.g., in U.S. Pat. No. 6,061,596 ("Method for Conditioning Pelvis Musculature Using an Implanted Microstimulator"); U.S. Pat. No. 6,051,017 ("Implantable Microstimulator and Systems Employing the Same"); U.S. Pat. No. 6,175,764 ("Implantable Microstimulator System for Producing Repeatable Patterns of Electrical Stimulation"); U.S. Pat. No. 6,181,965 ("Implantable Microstimulator System for Prevention of Disorders"); U.S. Pat. No. 6,185,455 ("Methods of Reducing the Incidence of Medical Complications Using Implantable Microstimulators"); and U.S. Pat. No. 6,214,032 ("System for Implanting a Microstimulator"). The '596, '017, '764, '965, '455, and '032 patents are incorporated herein by reference in their entireties.

Implantable stimulators having rechargeable batteries have specific requirements. In general once a stimulator is implanted within a patient's body, it is intended to stay there permanently. When a rechargeable battery is used to power an implantable stimulator, there must be a transcutaneous means to recharge the rechargeable battery in the stimulator without explanting the stimulator. In addition, there must also be a means to communicate with the stimulator after it has been implanted in order to transmit and receive control signals from and to the stimulator, as well as to transfer data from and to the stimulator. An important technical issue is how a rechargeable battery in an implanted stimulator may be revived when the rechargeable battery is completely depleted, i.e., to zero volts.

A specific form of an implantable stimulator is a microstimulator. Microstimulators present advantages over conventionally sized stimulators in that microstimulators are more easily implanted, with less surgical trauma. Advantageously, microstimulators may be injected through a large bore needle or placed via a small incision in the skin. In addition, microstimulators may be implanted in locations that do not offer enough space to contain larger, conventional-sized stimulators and their associated extension leads.

One application that is particularly suited for using a microstimulator is the treatment of urinary urge incontinence. The BION™ microstimulator is currently being used in patients to treat urinary urge incontinence by stimulating the pudendal nerve. In prior art implantable systems for treating incontinence, a conventional-size stimulator is attached to a lead having an electrode or electrodes on the distal lead tip. The lead, having a substantial length, can be tunneled to the target nerve deep inside the body, while the conventional-sized stimulator can remain implanted just beneath the surface of the skin. Because the conventional stimulator is intended to be placed just below the surface of the skin, the technical requirements for designing a telemetry communication system using such a conventional stimulator is, relatively speaking, easier to accomplish. Moreover, because the conventional-sized stimulator is in a comparatively large housing, such a stimulator can contain a primary, one-time-only-use battery and thus, no recharging is required.

An implantable microstimulator, in contrast, generally does not use an extension lead, as the electrodes are often placed directly on the body of the microstimulator. Because the electrodes are placed on the body of the microstimulator, it must usually be placed very close to the target tissue (usually a nerve) being stimulated. In the case of the urinary incontinence application, therefore, the microstimulator is implanted deep inside the body near the pudendal nerve and not, as in the case with conventional stimulators, just below the surface of the skin. In addition, when a microstimulator is used, the small housing puts the use of space at even a greater premium and effectively prohibits the use of a primary battery and, instead, necessitates the use of a rechargeable battery.

Thus, the technical challenges presented by a microstimulator that is implanted deep in the body are highly complex because (a) the microstimulator uses a rechargeable battery and (b) the microstimulator can be implanted more deeply and at variable depth within the body than a conventional stimulator. The variability of implantation depth can be problematic because the components that are used to charge the battery and communicate with the stimulator must accommodate this variability. Consequently, the technical requirements needed to fulfill the dual operations of transcutaneously recharging a battery and communicating with an implantable microstimulator are more daunting than using a conventional implantable stimulator, which merely requires near-distance telemetry communication and no charging circuitry. There are additional technical challenges to overcome when a microstimulator is placed deep in the body, for instance, in the lower part of the torso, as is the case for the urinary incontinence application. In particular, the external device configuration or configurations must be determined which can best recharge the battery in the microstimulator and communicate with the microstimulator. This set of technical requirements presents unique challenges in designing a charging and communication system which the present novel invention addresses.

SUMMARY OF THE INVENTION

The present invention addresses the above and other needs by providing an external charging and communication system that can be used with a deeply implanted stimulator or microstimulator having a rechargeable battery.

In accordance with one aspect of the invention, there is provided a charging and communication system that includes a chair pad (for sitting on) and a base station. The chair pad may include an antenna/charging coil for inductively charging the rechargeable battery and a booster coil for recharging the rechargeable battery when it has been inadvertently depleted to zero volts. The recharging from a base of zero volts is hereinafter termed "zero volt recovery" or "ZVR." A polyimide film substrate with copper traces is used as a grounded coil shield to cover the booster coil and antenna/charging coil in order to reduce the capacitively coupled currents to a patient and to prevent the occurrence of electric shock.

The booster coil and antenna/charging coil may be designed for charging and communications functions with a microstimulator that is implanted between 12 to 15 centimeters deep in the body with up to a 30.degree. off-axis misalignment from the microstimulator with the charging field. Inductive charging may be accomplished, for example, using a preferred frequency of 127 KHz.

In addition, the antenna/charging coil may be used for communication with the stimulator either employing frequency shift keying (FSK) or on-off keying (OOK) communication. FSK is akin to frequency modulated (FM) radio signals in that a radio frequency signal is conveyed through frequency modulation of a carrier signal. OOK may be compared to amplitude modulated (AM) radio signals in that the amplitude of a signal is modulated. However, unlike true AM signals, OOK communication permits only two amplitude levels: on or off, which amplitudes can convey the binary numbers 1 or 0. Data transfer with OOK communication is slow and therefore it is generally used only as a back-up when FSK communication is not available.

When the antenna/charging coil is used for FSK telemetry communication, it is necessary to tweak the bandwidth of the coil circuit to flatten or "dampen" the frequency response in order to broaden the bandwidth. This may be accomplished by connecting a damping resistor in parallel to the charging coil or by other circuit means. The damping resistor or other circuit means may be included in the base station.

The chair pad may contain a chair pad printed circuit board (PCB). The chair pad PCB may contain a temperature sensor such as a thermocouple to sense the temperature of the PCB and to send a signal to microcontroller to cut off power to the antenna/charging coil. The chair pad PCB may also contain a tuning circuitry for the antenna/charging coil to impedance match the charging coil with the amplifier in the base station and, similarly, the chair pad PCB may contain a tuning circuitry for the booster coil to impedance match the driving amplifier for the booster coil. Such impedance matching (tuning) is necessary to optimize the transfer of power from the base station amplifier to the coils and to reduce excess heat dissipation from the coils and, hence, from the chair pad, which excess heat would be undesirable. In addition, the impedance matching also contributes to reducing voltages and currents that are 1000 Volts and 4.5 Amperes, respectively in the base station, to a safer 0.5 Amperes and 25 volts in the antenna/charging coil, located in the chair pad. Thus, although in one embodiment of the present invention, the coils and amplifier may all be contained in a single, external interface device, the use of a separate base and external interface device (the chair pad) advantageously promotes a safer charging/communication system, by isolating the higher voltages and currents to the base station only.

The PCB may also contain protection circuits that include a temperature sensor and/or booster coil voltage sensing. The temperature sensor may be used to sense PCB temperature and when a predetermined temperature is reached, and automatic shut-off circuit may disconnect the power to the booster coil or antenna/charging coil to prevent overheating. Similarly, a voltage (or current) sensor may be used to sense the current and voltage in the booster or antenna/charging coils to calculate power dissipation and cut off power if it exceeds a predetermined trigger level. Such temperature and power monitoring features are desirable in the system, since the coils and circuitry are all contained in a coil assembly and encapsulated in a polyurethane foam housing, such that the circuitry cannot be directly accessed.

The base station is connectable via a chair pad cable to the chair pad. The base station is powered by an AC adapter. The base station may contain a microcontroller that can interface with visual displays such as LED and LCD displays mounted on the base station or with an audio alarm. The audio speaker may be used to produce sounds or tones to indicate when charging is complete or, alternatively, as a signal for other significant events. The microcontroller can be electrically connected to a coil driver amplifier, which microcontroller also controls the zero volt recovery charging and FSK and OOK communications. The base station contains a power converter section for generating several different values of D.C. voltages to supply power to the antenna/charging coil, the booster coil, the chair pad PCB, as well as circuitry in the base station.

The amplifier circuitry is provided in the base station in which a lower value +3.3 VDC is used in most cases, such as during charging, but is temporarily and briefly switchable to a +4.5 VDC during telemetry reception. Advantageously, this amplifier design reduces power consumption and thereby reduces the heat generated in the base station and also reduces switching regulator noise. A variable output +7 to +20 VDC power supply can be produced from the base station, which variable power may be continuously adjusted during inductive charging to prevent overheating.

It is thus a feature of the present invention to provide a charging and communication system that can be used both to charge the battery in the stimulator and to communicate with a stimulator implanted at a depth of between about 10 to 15 centimeters, while the stimulator is positioned up to 30 degrees off-axis relative to the inductive charging or RF telemetry field.

It is a further feature of the invention to provide impedance matching of the primary antenna/charging and booster coils with the driving amplifiers and also to adjust for misalignment of the primary coil with the secondary coil in the microstimulator to reduce heat dissipation in the base station and chair pad and to maximize power transfer.

It is another feature to include a zero-volt battery recovery system that can revive and recharge a battery that is fully depleted to zero-volts.

It is yet a further feature of the present system to provide fail-safe features to sense currents or voltages in the antenna/charging coil and booster coil or to directly sense temperatures on the chair pad PCB or on the base station PCB to automatically trigger power shut down to a coil to prevent overheating.

BRIEF DESCRIPTION OF THE DRAWINGS

The above and other aspects, features and advantages of the present invention will be more apparent from the following more particular description thereof, presented in conjunction with the following drawings wherein:

FIG. 4A is a view of the coil assembly in the chair pad;

FIG. 4B is an exploded view of the coil assembly of FIG. 4A;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

A fully assembled battery-powered microstimulator may operate independently, or in a coordinated manner with other implanted devices, or with external devices. For the purpose of describing the present invention, an exemplary microstimulator, the battery-powered BION™ microstimulator will be referred to interchangeably as a "microstimulator."

The microstimulator is a pulse generator which includes a rechargeable battery. The battery is recharged, as required, from an external battery charging system, typically through an inductive link. The microstimulator is preferably a substantially cylindrical shape and at least portions of it are hermetically sealed. The microstimulator may include electronic circuitry that allows it to generate stimulus pulses that are applied to a patient through electrodes.

The microstimulator circuitry, battery capacity, cycle life, hermeticity and longevity preferably provide implant operation for at least five years at typical settings. Battery control circuitry protects the battery from overcharging, operates the implant in a safe mode upon battery depletion and avoids any potentially endangering failure modes, with a zero tolerance for unsafe failure or operational modes. The microstimulator accepts programming only from compatible programming devices.

The publications and patents listed in the table below, which are all incorporated herein by reference, describe various uses of the implantable microstimulator for the purpose of treating various neurological conditions:

| Patent/Publication No. | Filing/Publication Date | Title |
| --- | --- | --- |
| U.S. Pat. No. 6,061,596 | Issued May 9, 2000 | Method for Conditioning Pelvic Musculature Using an Implanted Micrositmluator |

| Patent/Publication No. | Filing/Publication Date | Title |
| --- | --- | --- |
| U.S. Pat. No. 5,193,540 | Issued Mar. 16, 1993 | Structure and Method of Manufacture of an Implantable Micrositmluator |
| PCT Pub. WO 00/01320 | Pub. Jan. 13, 2000 | Implantable Stimulator System and Method for Treatment of Urinary Incontinence |
| PCT Pub. WO 97/18857 | Pub. May 29, 1997 | System and Method for Conditioning Pelvic Musculature Using an Implanted Micrositmluator |

Figure 1:
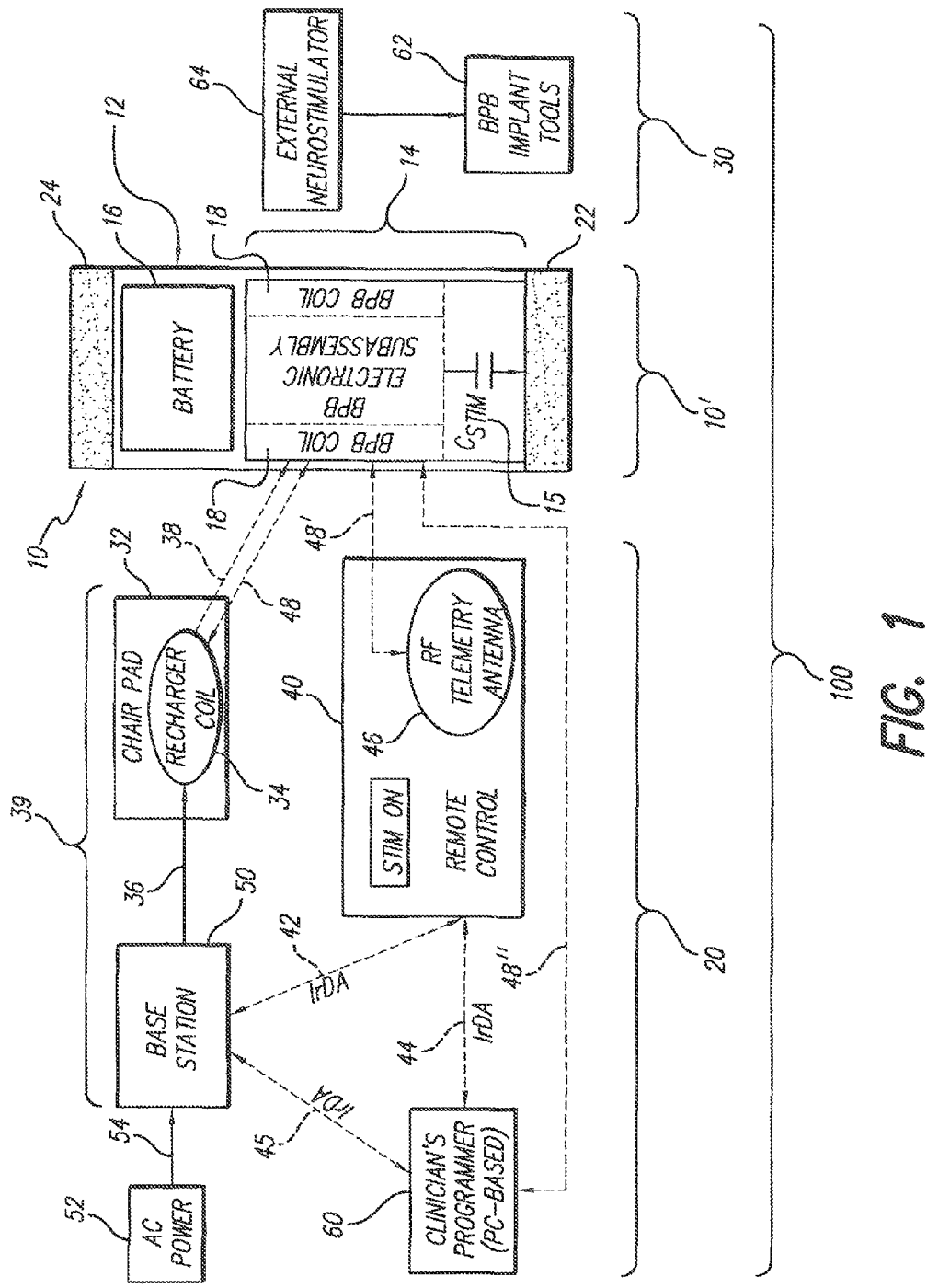
FIG. 1 is a block diagram of an exemplary microstimulator system, including an implantable microstimulator and various external components for charging the rechargeable battery in the microstimulator and communicating with the microstimulator.

FIG. 1 shows an exemplary, implantable, microstimulator system which includes internal and external components, as well as surgical components. Internal components 10' are implanted in the target tissue area of the patient and external components 20 are used to recharge and communicate with the internal components. The components shown in FIG. 1 represent, as a whole, an implantable BION™ microstimulator system 100 (also known as a Battery-Powered BION or "BPB"). As shown in FIG. 1, the various components may be subdivided into three broad categories: (1) implantable components 10', (2) external components 20, and (3) surgical components 30.

The microstimulator 10 includes a case 12; rechargeable battery 16; microstimulator electronic subassembly 14, which includes microstimulator coil 18 and a stimulating capacitor, $C_{STIM}$ 15; indifferent/reference electrode 24; and an active/stimulating electrode 22.

The external components 20 include a charging system 39, which consists of a chair pad 32 and a base station 50; a remote control 40; and a clinician's programmer 60. The chair pad 32 has an antenna/charging coil 34 which is electrically connectable to the base station 50 with extension 36 (or, alternatively, a chair pad cable) and communicates with the microstimulator electronic subassembly 14 with a bidirectional telemetry link 48. The base station 50 has an external, medical grade AC adapter which receives wall AC power 52 through an extension 54. The remote control 40 can send and receive communication from and to the base station 50 through an Infrared Data Association or IrDA interface 42. (IrDA is a standard for transmitting data via infrared light.) The remote control 40 also communicates with the clinician's programmer 60 through an IrDA interface 44 and communicates with the microstimulator electronic subassembly 14 with an RF telemetry antenna 46 through the bidirectional telemetry link 48'. The clinician's programmer 60 may also communicate with the microstimulator electronic subassembly 14 through the bidirectional telemetry link 48". The base station 50 also communicates with the clinician's programmer 60 through an IrDA interface 45. The bidirectional telemetry link 48 is also known as the FSK (Frequency Shift Key) telemetry link, or RF telemetry link. In addition, the charging system 39 has a forward telemetry link 38 which is also known as OOK-PWM (On/Off Keying—Pulse Width Modulation), or inductive telemetry link.

The surgical components 30 illustrated in FIG. 1 include the BPB implant tools 62 and an external neurostimulator 64. The implantable BPB microstimulator 10 is inserted through the patient's tissue through the use of appropriate surgical tools and, in particular, through the use of tunneling tools, as are known in the art or as are specially developed for purposes of implantable BPB stimulation systems.

Figures 1, 2:
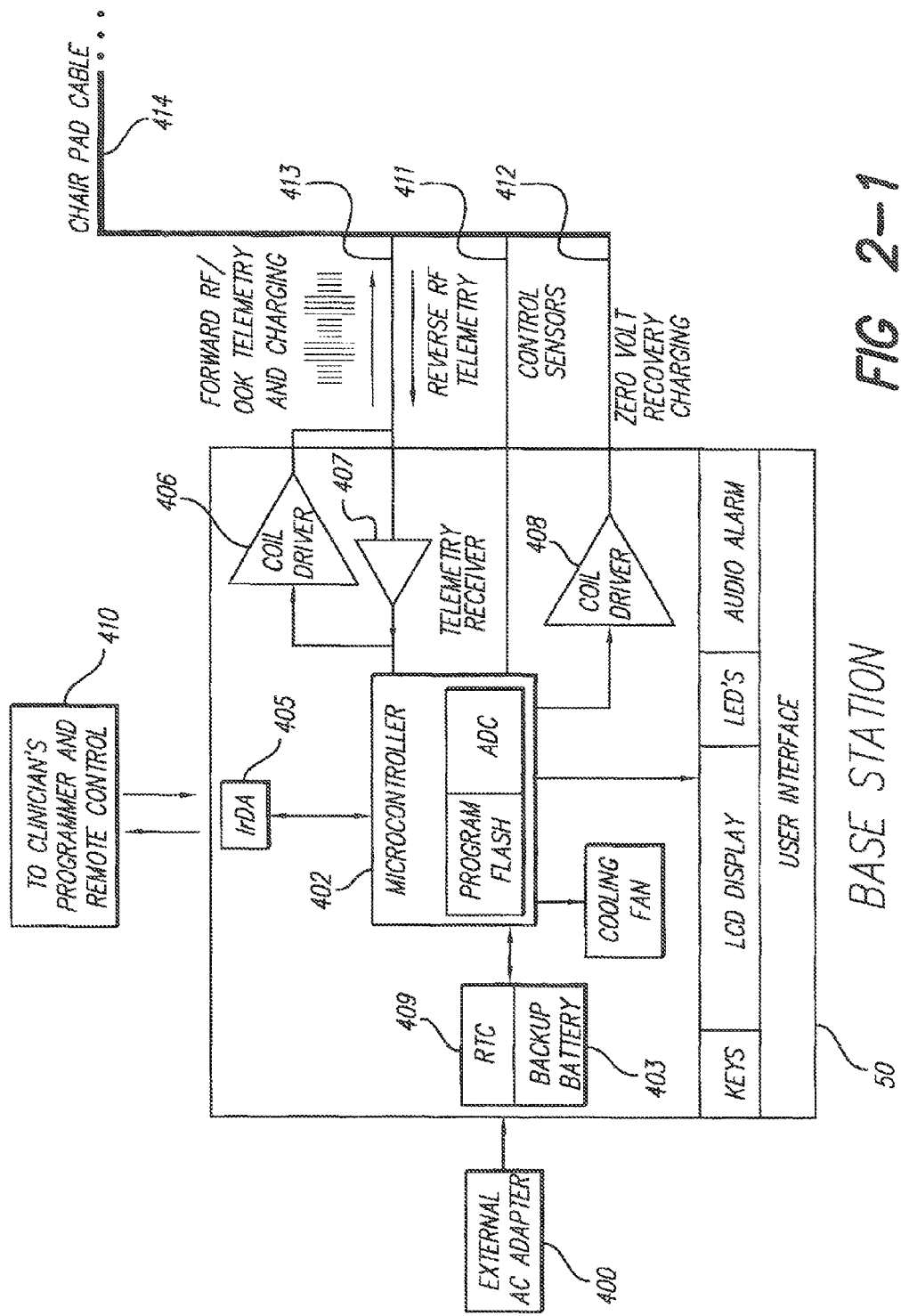
FIG. 2 (2-1; 2-2) is a view of a system that includes a base station and a chair pad, which system is used to charge the battery in the microstimulator and to communicate with the microstimulator.

FIG. 2 (2-1; 2-2) shows, in accordance with the present invention, a block diagram of a base station 50 and chair pad 32 charging and communication system. The base station is connected to the chair pad via a chair pad cable 414.

The base station/chair pad system is used to carry out four operations: (a) transcutaneously charging the rechargeable battery within the body implanted BPB stimulator using inductive coupling (b) transcutaneously providing recovery to the rechargeable battery in the BPB stimulator when the battery has been depleted down to zero volts, i.e., zero volt recovery (ZVR) (c) transcutaneously communicating with the BPB stimulator using frequency shift keying (FSK) and (d) transcutaneously communicating with the BPB stimulator using on-off keying (OOK).

The difference between operations (a) and (b) is that, in case (b), the rechargeable battery has been depleted down to zero volts. In that case, normal recharging will not work and it is necessary to use the ZVR procedure.

In order to enable the various operations, the chair pad 32, as shown in FIG. 2-2, has two coils: (a) an antenna/charging coil-34 and (b) a booster coil 419. The antenna/charging coil 34 is used for inductively charging the rechargeable battery in the stimulator and also for performing forward and backward FSK or forward OOK telemetry communication with the stimulator. The booster coil 419 is used to perform the ZVR procedure. The chair pad 32 further includes a coil shield 417 over the antenna/charging coil 34 and booster coil 419. Also included in the chair pad 32 is a chair pad printed circuit board (PCB) 416.

Referring to FIG. 2-1, an external AC adapter 400 is used to power the Base Station 50. The base station includes a battery backup 403 and a microcontroller 402 which can control the real-time clock (RTC) 409 and user interface displays such as user buttons/keys, LCD display(s), LED display(s) or an audio alarm. The audio alarm may be used to indicate when charging is complete or the alarm may be use as a signal indicator for other significant system events or modes. The microcontroller 402 is also connected to a coil driver amplifier 408 which controls the ZVR charging via connection 412 and the chair pad cable 414. In addition, the microcontroller 402 controls another coil driver 406 for controlling forward FSK and OOK telemetry communication and charging via connection 413 which is further connected to the chair pad cable 414. Through the same connection 413, reverse RF telemetry signals are received and amplified by telemetry receiver 407. These signals are then processed by the microcontroller 402. The microcontroller can communicate with an external clinician programmer 410 (or remote control) via an IrDA converter 405. The microcontroller may also receive data from various sensors via connection 411, which sensors may be located on the chair pad PCB 416. For instance, one type of sensor is a temperature sensor or a thermocouple.

Figure 3A:
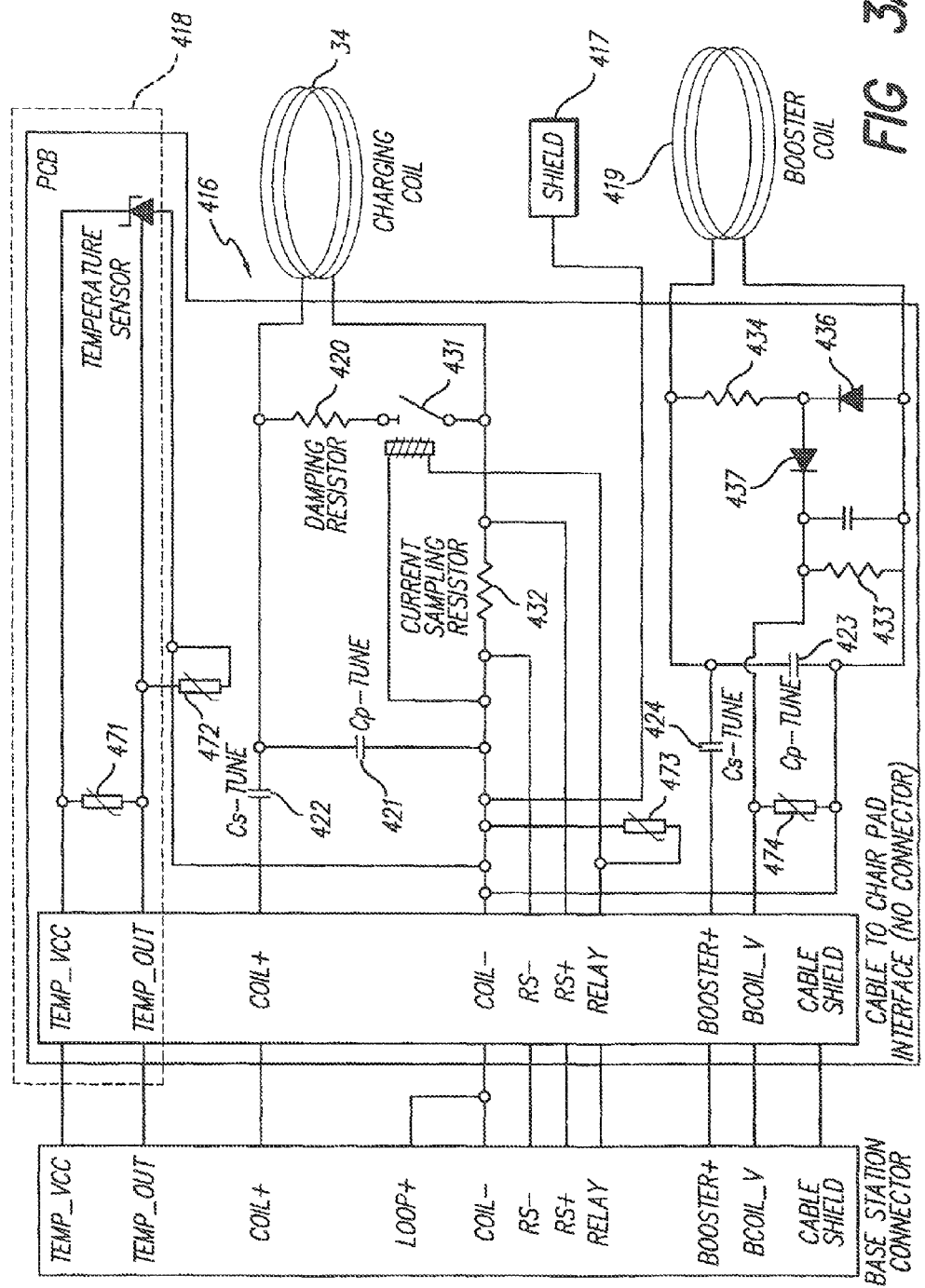
FIG. 3A is a simplified schematic diagram representing the electrical circuitry in the chair pad, including a printed circuit board.

FIG. 3A shows, in accordance with the present invention, a diagrammatic representation of the chair pad, electrical architecture. The representation shows the following chair pad components: a PCB board 416, the charging coil 34, the booster coil 419, and coil shield 417. The printed circuit board (PCB) 416 carries most of the chair pad electronics including a temperature sensor 418. The temperature sensor is used to ensure that the exterior surface of the chair pad 32 (shown in FIG. 3B) is at 41 degrees C. or less. The interior of the chair pad may, however, vary in temperature ranging from 0 degree to 65 degrees C.

All of the electronic components in the chair pad are contained on the chair pad PCB 416, with the exception of the antenna/charging coil 34, the booster coil 419 and coil shield 417. To ensure against electrical short circuit from moisture and liquids, the chair pad housing 633 (shown in FIG. 3B) contains all of the chair pad electrical components including the charging coil, the booster coil, and the chair pad PCB.

Figure 3B:
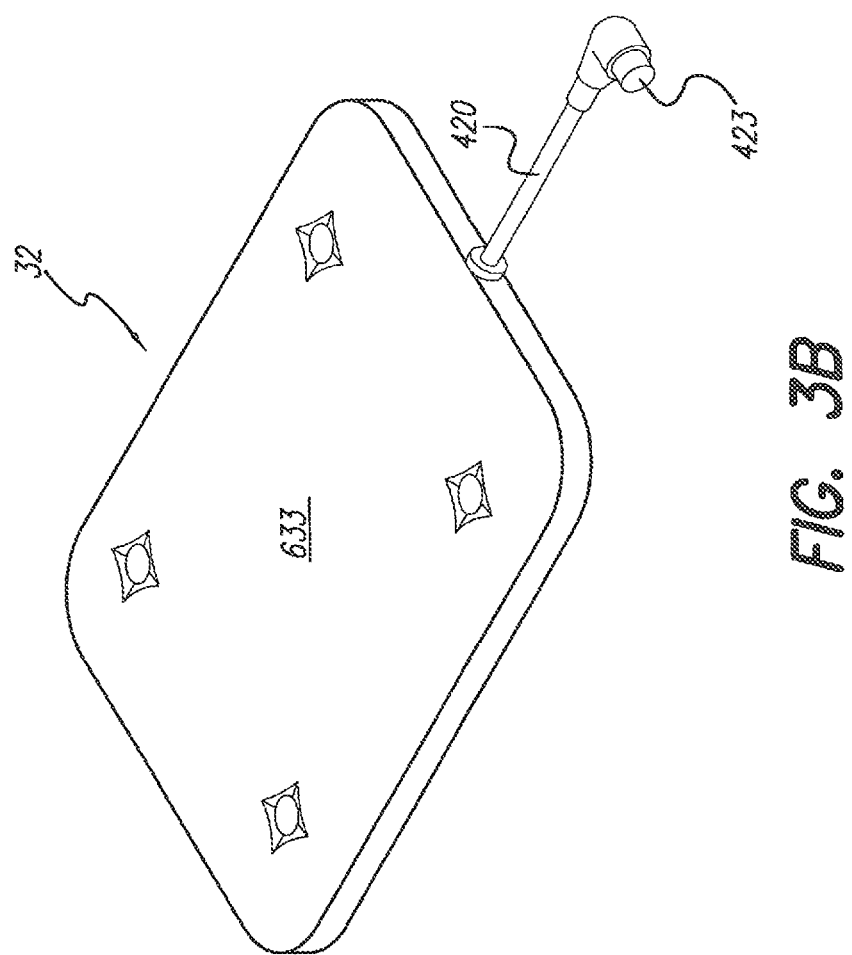
FIG. 3B is a mechanical representation of the exterior of the chair pad with a chair pad cable.

FIG. 3B shows, in accordance with the present invention, an illustration of the outer shape of the chair pad 32, which is approximately rectangular. The recharge coil assembly 427 (shown in FIG. 4A) contains the antenna/charging coil, the booster coil and a coil shield, which are all fully encapsulated in polyurethane foam housing 633 of chair pad 32. Because the coils are fully encapsulated by the foam housing 633, there are no access test points to verify that current is flowing in the charging and booster coils. The polyurethane foam housing provides a number of functions. For instance, the polyurethane foam housing 633 is UV resistant and flame retardant and forms a outer skin to keep Water and dust from the recharge coil assembly electronics. The foam housing also insulates the user from heat generated by the embedded electrical components in the chair pad and prevents the surface temperatures exterior to the polyurethane housing 633 (and the chair pad surface) from exceeding allowable surface temperatures. Further, the polyurethane housing protects the chair pad components from shock and vibration and contributes, in some measure with the outer padding, to provide a comfortable and compliant sitting surface. The chair pad housing 633 and electronics are preferably designed to meet a target chair pad surface temperature (including an outer padding around the chair pad foam housing 633) that is less than about 41 degrees C., without employing forced air-cooling or ventilation holes.

Padding may be placed around the polyurethane foam housing, which padding may be fabricated from a washable fabric or batting sewn together in a loose quilting format and be from about 0.75 inches to 1.00 inches in thickness in an uncompressed state. An exterior chair pad slipcover (not shown) may go over the padding. The slipcover may be constructed from a durable, washable upholstery grade fabric and should provide a relatively comfortable surface to sit on for extended periods of time, for instance, up to several hours. An opening in the slipcover should permit the cable to exit allow insertion of additional or replacement padding, when needed. Thus, although the foam housing, as shown in FIG. 3B, and coil assembly inside is, for the sake of simplicity, referred to herein as the "chair pad," it is emphasized that the actual "chair pad" used by a patient will usually include the extra padding and the slip cover.

The chair pad cable, 420 which is preferably longer than 150 cm, extends from the chair pad 32 and can be connected to the base station. The end of the cable can have a 24 pin male connector 423. The chair pad cable 420 can be molded into the polyurethane foam housing 633 to provide strain relief to the cable at the point of extension from the foam housing 633. In one embodiment, the chair pad may have dimensions which are about or smaller than 50 cm by 50 cm by 15 cm and weigh less than 5 kilograms. These are preferred dimensions and weight for the chair pad that work well for the average patient, although other pad shapes and dimensions may also work.

In use, the chair pad 32 may be placed on a chair and a patient, who has an implantable BPB microstimulator, can sit on the chair pad between about 15 minutes to half an hour a day to recharge the battery in the microstimulator. Generally, however, 15 minutes of charging may be sufficient.

FIG. 4A shows a mechanical illustration of a recharge coil assembly 427 with chair pad cable 420 having connector 423.

FIG. 4B shows a more detailed, exploded view of the components of the recharge coil assembly shown in FIG. 4A contained in the chair pad. The various components of the recharge coil assembly 427 include a cover 421 that may be made from injection molded polypropylene, a chair pad cable assembly 420 that links the chair pad to the base station, a coil spool 424, a shield flex circuit 425 ("coil shield") and a nest 426. Another coil shield 417 is used with shield 425 to "sandwich" the coil spool 424. The antenna/charging coil and booster coils are both contained in the coil spool 424 that is preferably made from injection molded polypropylene. Polypropylene is used for its low cost and excellent resistance to deformation under repetitive stress conditions.

The nest 426 is constructed from an injection-molded housing made from a polycarbonate-acrylonitrile butadiene styrene (PC/ABS) alloy. The nest is used to house the chair pad FR4 PCB assembly 422. Because it is necessary to minimize mechanical deflections of the PCB 422 to avoid damaging or loosening any of the circuit components, the nest 426 must be constructed of high strength and stiffness material to withstand compression/flexion loading of the recharge coil assembly 427. The box shape of the nest 426 enhances its stiffness. The PCB 422 is preferably at least about 0.093 inches thick to enhance its stiffness. In the complete coil assembly 427, the PCB is located between the nest 426 and the complementary rectangular portion of the cover 421.

The cover 421 is used to position the nest 426 and the spool 424 relative to each other. The assembled coil spool 424, cover 421 and nest 426 protect the coil spool 424 and the coils from being damaged by external objects that might penetrate through the polyurethane foam housing.

The coil shield flex circuit assemblies 417 and 425 ("coil shields") consist of polyimide film substrate with copper traces placed on one side and pressure sensitive adhesive on the opposite side. The coil shields 417 and 425 are preferably used to reduce the capacitively coupled currents to the patient and minimize the possibility of electric shock. The coil shields are grounded to provide a low impedance pathway to ground for the capacitively coupled currents generated in the antenna/charger coil and the booster coil, which operate at high voltages and frequencies. The coil shields 417 and 425 therefore reduce the leakage currents that can be induced in the patient during charging, telemetry and ZVR operations.

The flexible chair pad cable 420 with connector 423 may be permanently attached to the chair pad, with the connector 423 placed distal end of the cable. The base station housing can have a complementary female receptacle for connection to the chair pad. The chair pad cable connector 423 can also contain a loop back connection that is used to immediately indicate whether the chair pad is connected to the base station.

Through the connector 423 and chair pad cable 420, the base station can directly access the chair pad temperature sensor, the current sensing resistor of the charging coil, the voltage sensing circuitry of the booster coil, the relay for the FSK antenna operation of the charging coil, the chair pad connector feedback loop, chair pad cable shield and chair pad coil shield. In addition, the connector provides indirect access, through the particular tuning circuitries, to the charging coil and booster coil.

The chair pad cable 420 is shielded and may contain six twisted conductor pairs. In a preferred embodiment, five conductor pairs may be 26 AWG copper stranded construction containing 65 strands of 44 AWG tinned copper wire while the remaining conductor pair may be 24 AWG copper stranded construction containing 105 strands of 44 AWG tinned copper wires. The cable can be shielded with a circumferential braid of 40 AWG tinned copper strands with 90% minimum coverage. The cable jacket insulation may be a thermoplastic elastomer (TPE).

In the recharge coil assembly 427, the dimensions of the charging coil contained within the assembly may be optimized to deliver inductive coupled power to a microstimulator that is implanted deep in body tissue, for example, at an implant depth of between 12 to 15 centimeters and using a preferred frequency of about 127 KHz. To achieve these targets, the charging coil 34 preferably has 24 turns of multi-stranded Litz wire wrapped around the 200 mm inside diameter coil spool ("recharge coil spool"). The resulting diameter of charging coil is about 10 to 12 centimeters. The quality or Q of the resonant circuit is preferably about 160.

Referring to FIG. 2 (2-1; 2-2), in operation, the chair pad may be used to charge the rechargeable battery in the implanted stimulator. For normal microstimulator battery charging, i.e., where the rechargeable microstimulator battery has not be depleted down to zero volts, the base station 50 may power the charging coil 34 inside the chair pad 32, which generates a magnetic field and thereby inductively recharges the battery in the microstimulator.

To implement forward and reverse radio-frequency, FSK telemetry communication with the microstimulator, the charging coil 34 is used as an RF antenna. As an emergency back-up, forward OOK telemetry is also provided wherein the charging coil also operates as an antenna. The data transfer rate with OOK, however, occurs at a much lower rate than with FSK communication because, with OOK, the information is carried by on-off amplitude modulation.

Referring to FIG. 3A, in accordance with the present invention, the charging coil 34 can be used to generate a magnetic field of sufficient strength to inductively charge the microstimulator battery at a carrier frequency of 127 KHz. The maximum magnetic flux required along the microstimulator axis to achieve battery recharging at a rate of C/2 (half the maximum charge) is estimated to be 1.61 Gauss (rms) at 127 KHz. To achieve a recharging rate of C/8, the magnetic flux required is about 0.4 Gauss (rms). To achieve satisfactory charging at a microstimulator implant depth of between 10-15 centimeters inside a patient's body, the charging coil may be driven with a 4.25 Ampere (rms) current. The resulting magnetic flux of 0.93 Gauss (rms) can be produced at a point 15 cm vertically from the center plane of the charging coil, 5 cm radially away from its axis (maximum charging distance) and up to a 30 degree off-axis misalignment along the microstimulator, which magnetic flux can satisfactorily recharge the battery in the implanted microstimulator at the target charging distance. When a 4.25 Ampere (rms) current is applied to the charging coil, this can generate a magnetic flux of 1.81 Gauss (rms) at a point 10 cm vertically away from the center plane of the charging coil and 5 cm radially away from charging coil axis with up to a 30 degree off-axis misalignment. The resulting field can recharge the battery in approximately 2 hours.

The antenna/charging coil 34 may also be used for forward OOK telemetry, employing a narrow bandwidth around 333 Hz. When the antenna/charging coil is used, however, as an FSK antenna, it is necessary to increase the bandwidth. Bandwidth can be increased by connecting a damping resistor 420 (as shown in FIG. 3A) in parallel to the charging coil 34. By using the charging coil for RF and OOK telemetry communication, the base station can communicate with an implanted microstimulator. During such communication, the microstimulator with its internal coil may be centered at distances of 15 cm away from the chair pad charging coil.

An important function of the charging/communication system is the ability to recover the microstimulator when the rechargeable battery is completely dead. During such zero-volt recovery (ZVR), the microstimulator is defaulted to a depletion mode. A short duration, high amplitude magnetic field at a frequency of approximately 1.2 MHz is delivered to the microstimulator in order to set the microstimulator charging circuitry into a regular charging mode. The chair pad contains a booster coil 419 which is used to generate the short duration (less than 1 sec) magnetic field in the 1.2 MHz range.

In the event, however, that the microstimulator battery voltage should drop to a complete depletion level or "zero volt" mode, the microstimulator circuitry that controls the charging frequency will default to a state that causes the resonant frequency of the microstimulator circuitry and receiver coil to shift to about 1.2 MHz which is the Zero Volt Recovery (ZVR) frequency. Before normal charging of the microstimulator battery can begin, the base station temporarily operates in ZVR mode. In this ZVR mode, the booster coil is driven at the ZVR frequency (1.2 MHz), which resets the battery charging circuitry in the microstimulator to 127 KHz, by activating the front-end switches of the microstimulator setting the microstimulator to a trickle charge mode.

The booster coil 419 may have 6 turns of multi-stranded Litz wire in 2 layers of 3 turns each, wrapped around the charging coil inside the coil spool 424. The Litz wire used in the booster coil 419 can be the same kind used for the charging coil 34. The minimum magnetic flux required along the microstimulator longitudinal axis for ZVR is estimated to be 175 mGauss (rms) at 1.22 MHz.

Driving the booster coil at 2.9 Amperes (rms) can produce a magnetic flux of 175 mGauss (rms) at a point 15 cm vertically from the center plane of the booster coil, 5 cm radially away from the booster coil axis (the maximum ZVR distance) with up to 30o of axis misalignment relative to the microstimulator. This satisfies the ZVR distance between the chair pad and microstimulator. The chairpad can operate in this mode for more than 1 second.

As shown in FIG. 3A, the chair pad PCB 416 contains the circuitry required to interface with the coils 34, 419 and coil shield 417 and with the base. station which provides the power to drive the coils via the chair pad cable. The PCB 416 may contain the following circuits: temperature sensor 418 for the chair pad, a tuning circuitry for the charging coil, a tuning circuitry for the booster coil, a frequency damping system for the FSK telemetry antenna, a current sensing circuitry for the charging coil and a voltage sensing circuitry for the booster coil. Additionally, the PCB may contain electrostatic discharge (ESD) protection circuits 471, 472, 473 and 474 that are only active when electrostatic discharge is present.

Temperature sensing of the chair pad PCB is accomplished by employing a sensor such as an IC mounted thermocouple 418 to sense PCB temperatures in a range of between about 0.degree. to 100.degree. C. The temperature sensor 418 can monitor temperatures inside the PCB cavity that is, formed by the nest and cover. The base station is directly linked to this temperature sensor (Temp_Out) through the chair pad cable. (Temp_VCC indicates the VDC voltage supplied to the temperature sensor.)

As shown in FIG. 3A, the tuning components for the charging coil are placed on the chair pad PCB 416. The tuning components consist of two capacitors, a parallel capacitor (Cp-tune) 421 and a series capacitor (Cs-tune) 422 relative to the charging coil 34. These tuning capacitors are medical-grade, high voltage capacitors rated to operate above 1000 Volts (rms) and 4.25 Amperes (rms) at 127 KHz. These capacitors resonate the antenna/charging coil 34 at 127 KHz+/-6 KHz, when the coil is operated during battery charging, FSK telemetry or OOK telemetry. In addition to tuning the charging coil, the tuning capacitor circuitry provides an impedance matching network of 50 Ohms to the base station amplifier, when the coil is operated in inductive charging mode, thereby improving the efficiency of power transfer. In addition the impedance matching networks also contribute to reducing the voltage and current present in the charging coil to safer levels of 25 Volts at 0.5 Amperes, as compared to in the base station, where 1000 Volts at 4.5 Amperes are seen. In this way, the use of a separate base station and external interface device, in this instance the chair pad, contributes to a safer system, since higher voltages and currents are isolated to the separate base station.

Similarly, tuning components for the booster coil are placed on the chair pad PCB. The tuning components consist of two capacitors, a parallel capacitor (Cp-tune) 423 and a series capacitor (Cs-tune) 424, relative to the booster coil 419. The tuning capacitors are preferably medical-grade, high voltage capacitors rated to operate above 400 Volts (rms) and 3 Amperes (rms) at 1.2 MHz. These capacitors resonate the booster coil 419 at 1.2 MHz+/-0.1 MHz, when the coil is operated during ZVR. In addition to tuning the booster coil, the tuning capacitor circuitry provides an impedance matching network of 50 Ohms to the base station amplifier.

A damping system is required to broaden the available bandwidth, when the antenna/charging coil 34 operates as an FSK telemetry antenna. To accomplish this, a 2 KOhm damping resistor 420 may be connected in parallel to the charging coil 34 using a relay switch 431 rated for 2 Amperes. When the damping resistor 420 is connected in the charging coil circuit, the bandwidth of the charging coil circuit is increased to 12.37 KHz. The base station has direct control of the relay switch 431 and closes the circuit only during FSK telemetry operations. When the relay switch 431 is "open," the chair pad is in the charging mode.

Because there is no outside electrical access points to the charging coil or the booster coil, the system has means for measuring the coil currents or voltage (and, hence, the power) in the charging coil 34. In the charging mode, the current in the charging coil 34 is measured using the voltage across a 0.01 Ohm current sensing resistor 432 that is connected in series with the charging coil 34. The voltage across this resistor 432 is directly readable by the base station through the chair pad cable connector.

The voltage across the booster coil 419 is measured using a resistor voltage divider and rectifier circuit shown in FIG. 3A comprising diodes 436, 437 and resistors 434 and 433. The output signal of this voltage sensing circuitry is directly readable by the base station via the chair pad cable connector (at BCOIL_V).

Figure 5:
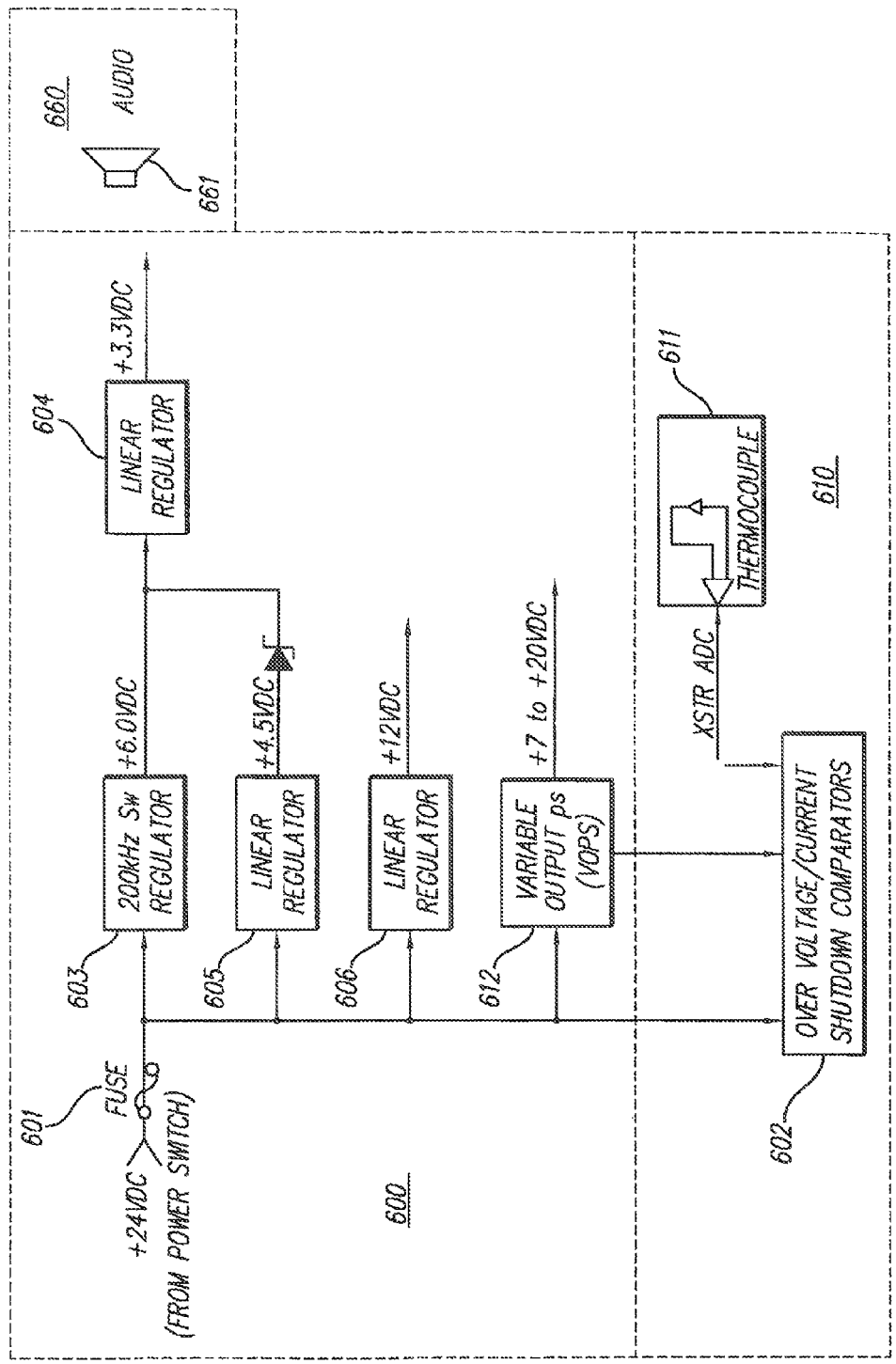
FIG. 5 is a block diagram of the power converter and shut down circuitry sections contained in the base station.

FIG. 5 depicts, in accordance with the present invention, a block diagram of the analog section of the battery charger in the base station, which includes three subsections, a power converter section 600, a shut-down circuit section 610 and an audio section 660. The shut-down circuitry represented by block 602 uses a comparator circuitry that is designed to trigger when a measured parameter (such as predetermined temperature level) exceeds 10%. A thermocouple 611 may be used as a temperature sensor. The audio circuitry section 660 employs a speaker 661 that can emit an audible tone or sound to signal a significant system event such as the end of charging.

In a preferred embodiment, the power converter section 600 generates several D.C. voltages from an input +24 VDC supplied by an external AC adapter. The +24 VDC input supply voltage passes through a power switch and through a 50 VDC, 2 ampere slow-blow type fuse 601. All charging electronics in the base station are connected after this slow blow fuse. The AC adapter voltage following the fuse 601 may be monitored by software such that when the voltage rises or falls 20% above or below the nominal +24 VDC, it is sensed by the over voltage/current shut-down comparators shown as block 602, thereby shutting down the coil driver amplifiers and power supply. The power converter section 600 generates a +3.3. VDC for the digital section of the battery charger, a +12 VDC for the analog section of the charger and telemetry analog sections (from linear regulator 606), and a high power variable output that ranges from +7 to +20 VDC for the coil driver power supply from variable output power source 612.

In order to minimize power consumption and reduce generation of heat, a switching regulator is preferably used for the digital circuitry. However, during communication with the microstimulator, the switching frequency may interfere with the telemetry reception on the telemetry PCB in the base station. Because of this, a +6.0 VDC is generated by a 200 KHz switching regulator 603 followed by a linear regulator 604 which produces +3.3 VDC. A parallel linear regulator 605 produces a +4.5 VDC which output is OR connected with the +6.0 VDC output. Linear regulator 605 is normally shut off when there is no communication. During normal operation, when there is no communication, both regulators are turned on. Since the switching regulator 603 voltage of +6.0 VDC is higher than the linear regulator 605 of the +4.5 VDC, the +6.0 VDC output provides most of the power, thereby providing more power more efficiently. During communication with the stimulator, which may occur once every minute, the +6.0 VDC switching regulator is turned off, allowing the +4.5 VDC linear regulator to provide power momentarily during the communication interval, which interval is typically less than a few seconds. This provides a less efficient, but a lower noise power generation during communication. Any loss of power efficiency during communication is not critical since it is only for a short duration.

Because the chair pad may not be located in exactly the same placement relative to the microstimulator during each inductive charging, the base station charging circuitry may be designed to automatically tune the charging circuit in order maximize power to the charging coil. This is accomplished by (a) maximizing the current in the charging coil and (b) maximizing the efficiency of the charging coil amplifier-within the base station section 600 by tuning the frequency.

The efficiency of an amplifier is defined as output power divided by input power. Input power to the amplifier is measured by the product of the input supply voltage multiplied by the input supply current. Both the input supply voltage and input supply current can be measured. The current to the charging coil may be measured by measuring a current sampling resistor that is placed in series with the charging coil. Since the current through, the sampling resistor is measured and known, the power dissipated by the charging coil can be obtained from the relation: power equals the square of the input current multiplied by the known coil resistor value. The tuning frequency may be software controlled.

During inductive charging of the rechargeable battery, it may be necessary to reduce the charge field strength caused by induced eddy currents in the stimulator case to prevent overheating. To accomplish this, the variable output power supply 612 may be used. In the example shown, a +7 to +20 VDC may be selectable in 100 step increments.

Figure 6:
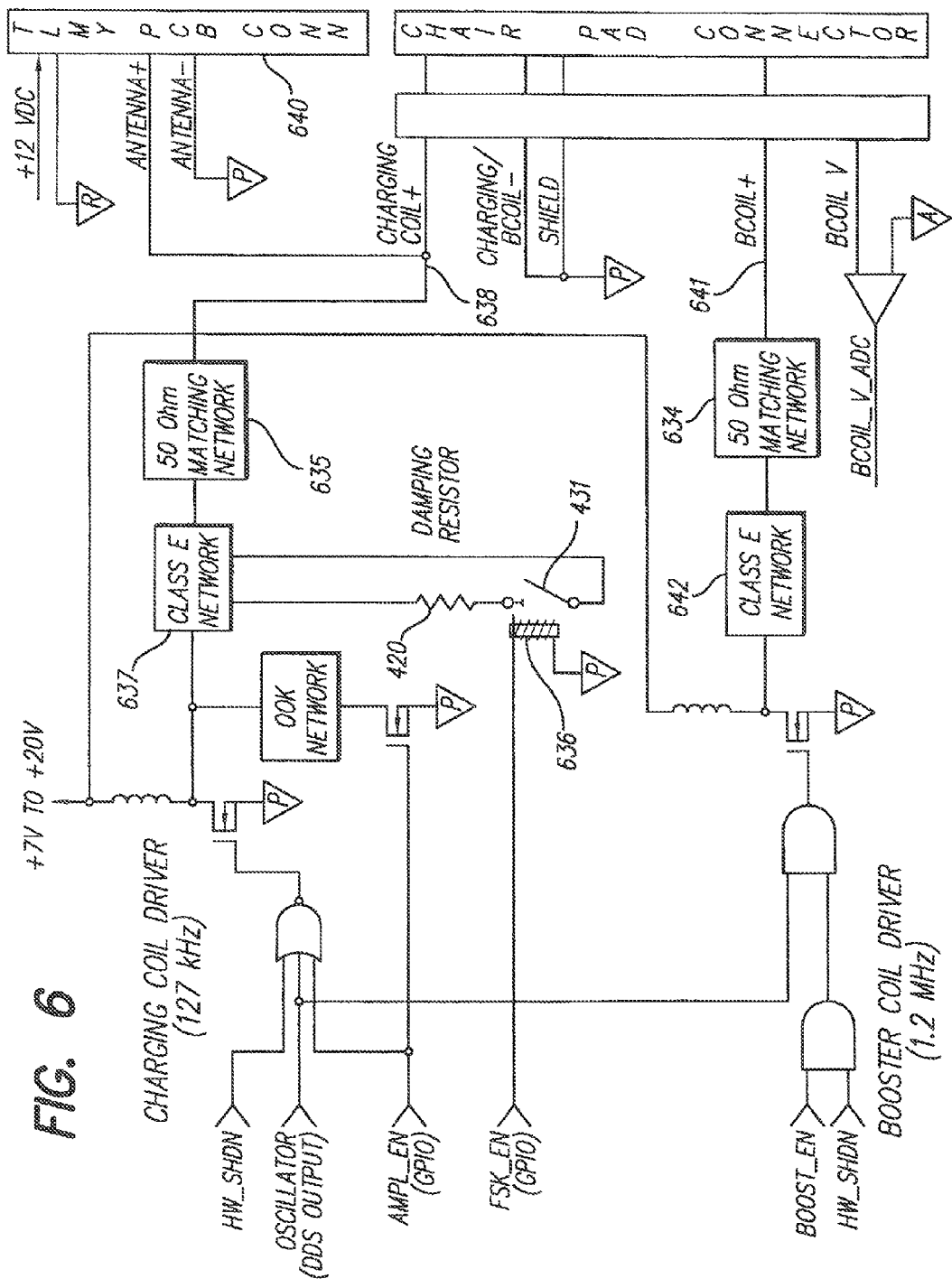
FIG. 6 is a block diagram of power supply drivers for the antenna/charging coil and booster coil contained in the base station.

FIG. 6 shows, in accordance with the present invention, a block diagram of the battery charger PCB analog section for the coil drivers located in the base station. A charging coil driver is required to provide forward and reverse FSK telemetry to the microstimulator within a carrier frequency, preferable in the range of 121 to 133 KHz, and a modulating signal frequency range of +/−4 KHz. To obtain FSK telemetry, an amplifier in the base station must drive the antenna/charging coil via connection 638. To increase the bandwidth, the Q of the charging coil and amplifier filter inductance is reduced to approximately about 10. During FSK communication (both transmit and receive), a software-controlled switch relay 431 is used to connect a damping resistor 420 in parallel to the charging coil and the amplifier inductor 636. Reverse FSK telemetry is also received via the damped charging coil 636. The receiver on the telemetry PCB connector 640 interfaces with a 50 Ohm impedance matching network 635.

For OOK operation, the battery charger is required to amplitude modulate the charge field at a maximum rate of 166 beats per second. This can be implemented by enabling and disabling the amplifier at the required data rate. Because the amplifier is impedance matched with the chair pad coil while the amplifier is active, power can be efficiently transferred to the coil. However, when the amplifier is turned off, the impedance matching is poor and can result in a sub-optimal power transfer out of the coil and a slow fall time. To improve the data transfer rate of the amplifier when the amplifier is turned off, the impedance matching network 635 is switched on using a transistor at the input of the class E network 637. This restores the 50 Ohm impedance matching between the amplifier network and charging coil while the amplifier is off and produces maximum power transfer out of the coil at an increased data rate. While the amplifier is turned on, the OOK network is switched out of the Class E network and is not operational during that time.

The booster coil amplifier is required to drive the chair pad booster coil via connection 641 with sufficient power to re-initialize the battery charger tuning circuitry in the stimulator to 127 KHz during ZVR, while the charging coil in the chair pad is at a maximum vertical separation distance of 15 cm from the microstimulator with a maximum horizontal offset from the center axis of the booster coil of 5 cm. The estimated power to the coil necessary to achieve re-initialization is approximately 11.25 Watts at 1.2 MHz. The booster coil amplifier may be designed to drive the booster coil with a maximum power of 20 Watts at 1.2 MHz. The booster coil amplifier power can be adjusted using the same variable DC/DC converter used for the charging coil amplifier.

Automatic tuning (impedance matching) is used to maximize the efficiency and power to the booster coil in the same manner as used for the charging coil. A 50 Ohm impedance matching network 634 may be used in the booster coil amplifier circuit that is placed serial to a class E amplifier network 642. The identical method that is used to measure input power to the charging coil amplifier is also used for the booster coil amplifier. The booster coil voltage is measured using a simple voltage divider and rectifier circuit in the chair pad. This voltage is monitored and used to calculate output power to the booster coil.

It can be appreciated that the charger and communications system comprising the chair pad and base station have been discussed in the context of charging and communicating with a microstimulator such as a BPB microstimulator. However, such a charging and communication system may be employed with any implanted stimulator that is larger in size, than a microstimulator. In general, a BPB microstimulator does not exceed a maximum lengthwise dimension of about 3.5 cm and has a width that is appreciably smaller, e.g., less than about 5 mm.

Furthermore, the charging and communication system of the present invention may also be adapted for use for other external device configurations. For example, instead of a chair pad, the electronic components may be used in an external charging/communications device (an "external interface" device) that is to be placed over other parts of the body, such as the back, over a limb, such as an arm or leg, or over the surface of the head. When used for the head, the chair pad may, instead, be configured and used as a pillow. The general concepts employed and components used inside the chair pad may readily be adapted for use in a pillow or other external charging/communications device.

In yet a further embodiment of the present invention, the external charging/communications component may integrate those components included in the chair pad, e.g., the booster coil, the antenna/charging coil and chair pad PCB with components that are in the base station, such as the power converter, shut-off safety circuitry and the microcontroller, thereby eliminating a separate base station device in the system.

While the invention herein disclosed has been described by means of specific embodiments and applications thereof, numerous modifications and variations could be made thereto by those skilled in the art without departing from the scope of the invention set forth in the claims.

The invention claimed is:

1. A system comprising:
   an implantable medical device, comprising a rechargeable battery and charging circuitry configured for charging the rechargeable battery; and
   an external device, comprising;
      a first coil, wherein the first coil is configured to transmit first magnetic field to inductively charge the rechargeable battery within the implantable medical device;
      a second coil, wherein the second coil is configured to temporarily transmit a second magnetic field to recover the implantable medical device when the rechargeable battery is depleted to zero volts; and
   wherein when the rechargeable battery is depleted to zero volts, the implantable medical device is configured to use the received second magnetic field to recover the implant by setting the charging circuitry into a regular charging mode during which the charging circuitry can use the first magnetic field to charge the battery.

2. The system of claim 1, wherein the first coil is also configured to communicate with the implantable medical device.

3. The system of claim 2, wherein the first coil communicates with the implantable medical device using frequency shift keying (FSK) telemetry.

4. The system of claim 2, wherein the first coil communicates with the implantable medical device using on-off keying (OOK) telemetry.

5. The system of claim 1, wherein the external device further comprises current measuring circuitry for determining power consumption in the first coil.

6. The system of claim 1, wherein the external device further comprises a printed circuit board (PCB) coupled to the first coil and to the second coil.

7. The system of claim 6, wherein the external device further comprises sensing circuitry on the PCB for sensing temperature.

8. The system of claim 7, wherein the external device further comprises tomatic power shut-off circuitry for automatically shutting off power to the first coil when the sensed temperature exceeds a predetermined level.

9. The system of claim 1, wherein the external device further comprises automatic power shut-off circuitry for automatically shutting off power to the first coil when the power consumption through the first coil exceeds a predetermined level.

10. The system of claim 1, wherein the external device further comprises automatic power shut-off circuitry for automatically shutting off power to the second coil when the power consumption through the second coil exceeds a predetermined level.

11. The system of claim 1, wherein the second coil has a plurality of turns of wire in a plurality of layers wrapped around a coil spool.

12. The system of claim 1, wherein the external device comprises a chair pad.

13. The system of claim 1, wherein the external device is comprised of a compliant material.

14. The system of claim 1, further comprising an exterior slipcover that surrounds the external device.

15. The system of claim 1, wherein the external device further comprises a coil assembly containing the second coil and the first coil.

16. The system of claim 1, wherein the system further comprises a base station coupled to the external device by a cable for controlling the first coil and the second coil.

* * * * *